United States Patent
Hou

(10) Patent No.: US 10,751,011 B2
(45) Date of Patent: Aug. 25, 2020

(54) MEDICAL IMAGING DEVICE AND SUSPENSION GANTRY INCLUDING MULTIPLE ROTATABLE ARMS

(71) Applicant: Beijing Neusoft Medical Equipment Co., Ltd., Beijing (CN)

(72) Inventor: Xiaofeng Hou, Shenyang (CN)

(73) Assignee: Beijing Neusoft Medical Equipment Co., Ltd., Beijing (CN)

( * ) Notice: Subject to any disclaimer, the term of this patent is extended or adjusted under 35 U.S.C. 154(b) by 296 days.

(21) Appl. No.: 15/476,518

(22) Filed: Mar. 31, 2017

(65) Prior Publication Data
US 2017/0347981 A1  Dec. 7, 2017

(30) Foreign Application Priority Data

Jun. 3, 2016  (CN) .......................... 2016 1 0390881
Jan. 25, 2017  (CN) .......................... 2017 1 0056672

(51) Int. Cl.
*A61B 6/00* (2006.01)

(52) U.S. Cl.
CPC .......... *A61B 6/4441* (2013.01); *A61B 6/4429* (2013.01); *A61B 6/4435* (2013.01); *A61B 6/4447* (2013.01); *A61B 6/4464* (2013.01)

(58) Field of Classification Search
CPC ... A61B 6/4435; A61B 6/4441; A61B 6/4447; A61B 6/44; A61B 6/4405; A61B 6/4429; A61B 6/4411; A61B 6/4464
USPC ................................................. 378/196–198
See application file for complete search history.

(56) References Cited

U.S. PATENT DOCUMENTS

| | | | | |
|---|---|---|---|---|
| 6,813,334 | B2* | 11/2004 | Koppe | A61B 6/025 378/21 |
| 6,869,217 | B2* | 3/2005 | Rasche | A61B 6/4441 378/193 |
| 7,018,097 | B2* | 3/2006 | Schmitt | A61B 6/4441 378/197 |
| 7,130,378 | B2* | 10/2006 | Akutsu | A61B 6/10 378/117 |

(Continued)

FOREIGN PATENT DOCUMENTS

| CN | 102065767 A | 5/2011 |
|---|---|---|
| CN | 103143124 A | 6/2013 |

(Continued)

OTHER PUBLICATIONS

An English translation of CN102065767A by Patent Translate.*

(Continued)

*Primary Examiner* — Allen C. Ho
(74) *Attorney, Agent, or Firm* — Fish & Richardson P.C.

(57) ABSTRACT

The present disclosure discloses medical imaging devices and suspension gantries thereof. An example medical imaging device includes a suspension gantry and a rotatable C-arm which is connected with the suspension gantry and provided with an imaging chain. The suspension gantry includes a suspension base, a first rotating arm configured to be connected to the suspension base and rotatable around a first axis, and a second rotating arm configured to be connected to the first rotating arm and rotatable around a second axis. The rotatable C-arm is configured to be connected with the second rotating arm and be rotated around a third axis.

20 Claims, 10 Drawing Sheets

(56) References Cited

U.S. PATENT DOCUMENTS

| | | | | |
|---|---|---|---|---|
| 7,168,855 B2* | 1/2007 | Engström | A61B 6/4441 | 378/196 |
| 7,220,052 B2* | 5/2007 | Gotoh | A61B 6/02 | 378/193 |
| 7,246,943 B2* | 7/2007 | Gotoh | A61B 6/4014 | 378/196 |
| 7,267,482 B2* | 9/2007 | Ohishi | A61B 6/4441 | 378/196 |
| 7,269,246 B2* | 9/2007 | Ohishi | A61B 6/481 | 378/196 |
| 7,341,375 B2* | 3/2008 | Zaiki | A61B 6/0457 | 378/196 |
| 7,478,949 B2* | 1/2009 | Niessen | A61B 6/08 | 378/197 |
| 7,500,783 B2* | 3/2009 | Kalender | A61B 6/032 | 378/197 |
| 7,534,036 B2* | 5/2009 | Delmas | A61B 6/4441 | 378/196 |
| 7,578,618 B2* | 8/2009 | Timmermans | A61B 6/4441 | 378/197 |
| 7,591,587 B2* | 9/2009 | Gotoh | A61B 6/4441 | 378/189 |
| 7,594,751 B2* | 9/2009 | Grebner | A61B 6/4014 | 378/196 |
| 7,634,308 B2* | 12/2009 | Ogawa | A61B 6/481 | 378/196 |
| 7,697,740 B2* | 4/2010 | Fujisawa | A61B 6/032 | 378/95 |
| 7,874,727 B2* | 1/2011 | Forster | E06B 9/264 | 378/196 |
| 7,991,118 B2* | 8/2011 | Noordhoek | A61B 6/4441 | 378/115 |
| 8,121,255 B2* | 2/2012 | Sugiyama | A61B 6/4441 | 378/42 |
| 8,351,574 B2* | 1/2013 | Takemoto | A61B 5/02007 | 378/4 |
| 8,408,788 B2* | 4/2013 | Ozawa | A61B 6/102 | 378/197 |
| 8,534,915 B2* | 9/2013 | Maschke | A61B 6/4411 | 378/196 |
| 8,542,891 B2* | 9/2013 | Yokota | A61B 6/12 | 378/98.11 |
| 8,591,107 B2* | 11/2013 | Peters | A61B 6/4441 | 378/193 |
| 8,764,291 B2* | 7/2014 | Ruijters | A61B 5/06 | 378/195 |
| 8,767,909 B2* | 7/2014 | Vogtmeier | A61B 6/025 | 378/193 |
| 8,781,068 B2* | 7/2014 | Noda | A61B 6/4233 | 378/19 |
| 8,794,832 B2* | 8/2014 | Noda | A61B 6/4441 | 378/193 |
| 8,923,593 B2* | 12/2014 | Florent | G06T 7/337 | 382/132 |
| 8,944,680 B2* | 2/2015 | Graumann | A61B 6/4452 | 250/491.1 |
| 9,173,628 B2* | 11/2015 | Bouvier | A61B 6/4405 | |
| 9,220,471 B2* | 12/2015 | Noda | A61B 6/4233 | |
| 9,478,018 B2* | 10/2016 | Rongen | A61B 6/4441 | |
| 9,480,437 B2* | 11/2016 | Watanabe | A61B 6/022 | |
| 9,492,137 B2* | 11/2016 | Iwamoto | A61B 6/4283 | |
| 9,532,757 B2* | 1/2017 | Claus | A61B 6/4441 | |
| 9,625,581 B2* | 4/2017 | Chang | B29C 64/20 | |
| 9,655,585 B2* | 5/2017 | Watanabe | A61B 6/542 | |
| 9,737,275 B2* | 8/2017 | Noda | A61B 6/4441 | |
| 9,801,598 B2* | 10/2017 | Zaiki | A61B 6/4441 | |
| 9,851,708 B2* | 12/2017 | Heijman | H03K 17/975 | |
| 9,855,016 B2* | 1/2018 | Lee | A61B 6/4441 | |
| 9,855,446 B2* | 1/2018 | Chang | A61N 5/1084 | |
| 9,875,531 B2* | 1/2018 | Goossen | A61B 6/12 | |
| 9,888,892 B2* | 2/2018 | Abe | A61B 6/466 | |
| 9,895,559 B2* | 2/2018 | Chang | A61B 34/30 | |
| 9,904,978 B2* | 2/2018 | Florent | A61B 6/487 | |
| 9,913,623 B2* | 3/2018 | Ohishi | A61B 6/4441 | |
| 9,928,618 B2* | 3/2018 | Lee | A61B 6/06 | |
| 9,931,091 B2* | 4/2018 | Watanabe | A61B 6/463 | |
| 9,936,928 B2* | 4/2018 | Wakai | A61B 6/487 | |
| 9,962,139 B2* | 5/2018 | Kojima | A61B 6/0457 | |
| 9,986,959 B2* | 6/2018 | Atzinger | A61B 6/4441 | |
| 9,997,269 B2* | 6/2018 | Roh | A61B 6/405 | |
| 10,071,265 B2* | 9/2018 | Chang | A61B 6/4458 | |
| 10,080,532 B2* | 9/2018 | Ohishi | A61B 6/487 | |
| 10,080,536 B2* | 9/2018 | Margot | A61B 6/4405 | |
| 10,172,574 B2* | 1/2019 | Schäfer | A61B 6/02 | |
| 10,219,776 B2* | 3/2019 | Belei | A61B 6/0457 | |
| 10,271,804 B2* | 4/2019 | Ohga | A61B 6/469 | |
| 10,271,808 B2* | 4/2019 | Auvray | A61B 6/032 | |
| 10,285,660 B2* | 5/2019 | Zaiki | A61B 6/4429 | |
| 10,368,816 B2* | 8/2019 | Bouvier | A61B 6/10 | |
| 10,405,821 B2* | 9/2019 | Hansis | A61B 5/4566 | |
| 10,413,260 B2* | 9/2019 | Bouvier | A61B 6/105 | |
| 10,506,997 B2* | 12/2019 | Fuchigami | A61B 6/487 | |
| 2004/0008820 A1 | 1/2004 | Schmitt | | |
| 2008/0075225 A1 | 3/2008 | Kalender | | |
| 2011/0280379 A1 | 11/2011 | Maschke | | |

FOREIGN PATENT DOCUMENTS

| | | |
|---|---|---|
| CN | 103813751 A | 5/2014 |
| CN | 204863241 U | 12/2015 |
| CN | 204909477 U | 12/2015 |
| CN | 206228357 U | 6/2017 |

OTHER PUBLICATIONS

An English translation of CN103143124A by Patent Translate.*
An English translation of CN204863241U by Patent Translate.*
State Intellectual Property Office of the People's Republic of China, Office Action and Search Report Issued in counterpart Chinese Patent Application No. 201710056672.8 (dated Mar. 22, 2019), 16 pages. (submitted with English-language machine translation).
State Intellectual Property Office of the People's Republic of China; Office Action and Search Report issued in counterpart Chinese Application No. 201710056672.8 (dated Jan. 2, 2020) 15 pages. (with English-language machine translation).
State Intellectual Property Office of the People's Republic of China, Office Action and Search Report Issued in Application No. 201710056672.8, dated Jun. 12, 2020, 23 pages, (Submitted with Machine Translation).

* cited by examiner

MEDICAL IMAGING DEVICE AND SUSPENSION GANTRY INCLUDING MULTIPLE ROTATABLE ARMS

CROSS REFERENCE TO RELATED APPLICATIONS

This application claims priority under 35 U.S.C. § 119 to Chinese Patent Application No. 201610390881.1, filed on Jun. 3, 2016, the entire content of which is incorporated herein by reference.

TECHNICAL FIELD

The present disclosure relates to medical imaging devices and suspension gantries thereof.

BACKGROUND

At present, a common medical imaging device may be an X-ray medical imaging device. A large-scale real-time X-ray medical imaging device, such as an angiographic machine, may complete the imaging of blood vessels in various parts of a body such as cardiovascular, cerebrovascular, aorta, blood vessels of abdominal organs, pelvic blood vessels, blood vessels of limbs, etc. Imaging results may have a diagnostic value to vascular lesions, tumor lesions and the like of various parts of the body. The angiographic machine may also assist in the interventional treatment of lesions in various parts of the body, such as vascular embolization of liver cancer, perfusion chemotherapy of lung cancer, embolization of cerebral aneurysm, embolization of cerebral arteriovenous malformations, balloon dilatation and stent implantation of coronary artery stenosis, occlusion of atrial septal defect and patent ductus arteriosus of congenital heart disease, balloon dilatation of mitral valve and pulmonary stenosis, dilatation and stent implantation of biliary tract and oesophagus, a variety of percutaneous biopsy and drainage, and other advanced interventional surgeries.

SUMMARY

The present disclosure provides medical imaging devices and corresponding gantries, which can satisfy more clinical application requirements.

One aspect of the present disclosure features a suspension gantry that can be connected with a rotatable C-arm having an imaging chain. The suspension gantry includes: a suspension base, a first rotating arm configured to be connected to the suspension base and rotatable around a first axis, and a second rotating arm configured to be connected to the first rotating arm and rotatable around a second axis. The rotatable C-arm is configured to be connected with the second rotating arm and be rotated around a third axis.

In some implementations, the first axis is perpendicular to an interface contacting the first rotating arm and the suspension base; the second axis is perpendicular to an interface contacting the second rotating arm and the first rotating arm; the second rotating arm is connected to a first end of the first rotating arm and the suspension base is connected to a second end of the first rotating arm which is opposite to the first end; and the first axis and the second axis are spaced with a distance. In some cases, the third axis is perpendicular to an interface contacting the rotatable C-arm and the second rotating arm, and the rotatable C-arm is connected to a first end of the second rotating arm and the first rotating arm is connected to a second end of the second rotating arm which is opposite to the first end. In some cases, the first axis is parallel to the second axis, and the third axis is perpendicular to the first axis and the second axis.

The first rotating arm can include an inclined portion which inclines from an end of the first rotating arm to which the suspension base is connected towards another end of the first rotating arm to which the second rotating arm is connected. The second rotating arm can include a bending portion between a first end and a second end of the second rotating arm. The first rotating arm can include a bending portion between a first end and a second end of the first rotating arm. The suspension gantry can further include a guide rail mounted on a top of an operating room; and a crane mounted on the guide rail and configured to be movable along the guide rail, the suspension base being mounted on the crane.

In some implementations, the suspension gantry further includes a supporting base, and the suspension base is mounted on the supporting base and rotatable around a fourth axis. In some cases, the fourth axis is disposed at a first end of the suspension base and the first rotating arm is connected to a second end of the suspension base which is opposite to the first end; and a plane in which the fourth axis is located is perpendicular to the first axis.

The suspension gantry can further include a supporting frame, and the supporting base is mounted on the supporting frame. The suspension gantry can further include a height adjusting device disposed between the supporting base and the supporting frame. The suspension gantry can further include a guide rail mounted at an upper end of the supporting frame and a wheel set mounted on the guide rail and configured to be movable along the guide rail, the supporting base and the wheel set forming a crane, the suspension base being mounted on the crane and rotatable around the fourth axis.

Another aspect of the present disclosure features a medical imaging device including a suspension gantry and a rotatable C-arm. The suspension gantry includes a suspension base, a first rotating arm configured to be connected to the suspension base and rotatable around a first axis, and a second rotating arm configured to be connected to the first rotating arm and rotatable around a second axis. The rotatable C-arm is configured to be connected with the second rotating arm and rotated around a third axis, the rotatable C-arm being provided with an imaging chain.

In some implementations, the first axis is perpendicular to an interface contacting the first rotating arm and the suspension base; the second axis is perpendicular to an interface contacting the second rotating arm and the first rotating arm; the second rotating arm is connected to a first end of the first rotating arm and the suspension base is connected to a second end of the first rotating arm which is opposite to the first end; and the first axis and the second axis are spaced with a distance. In some cases, the third axis is perpendicular to an interface contacting the rotatable C-arm and the second rotating arm; and the rotatable C-arm is connected to a first end of the second rotating arm and the first rotating arm is connected to a second end of the second rotating arm which is opposite to the first end. In some cases, the first axis is parallel to the second axis; and the third axis is perpendicular to the first axis and the second axis.

In some examples, the first rotating arm includes an inclined portion which inclines from an end of the first rotating arm to which the suspension base is connected towards another end of the first rotating arm to which the second rotating arm is connected. In some examples, the second rotating arm includes a bending portion between a first end and a second end of the second rotating arm. In some examples, the first rotating arm includes a bending portion between a first end and a second end of the first rotating arm. In some examples, the suspension gantry further includes: a guide rail mounted on a top of an operating room; and a crane mounted on the guide rail and configured to be movable along the guide rail, the suspension base being mounted on the crane.

In some implementations, the suspension gantry includes a supporting base, and the suspension base is mounted on the supporting base and rotatable around a fourth axis. In some examples, the fourth axis is disposed at a first end of the suspension base and the first rotating arm is connected to a second end of the suspension base which is opposite to the first end; and a plane in which the fourth axis is located is perpendicular to the first axis.

In some implementations, the suspension gantry includes a supporting frame, and the supporting base is mounted on the supporting frame. In some examples, the suspension gantry further includes a height adjusting device disposed between the supporting base and the supporting frame. In some examples, the suspension gantry further includes a guide rail mounted at an upper end of the support frame; and a wheel set mounted on the guide rail and configured to be movable along the guide rail, the supporting base and the wheel set forming a crane, the suspension base being mounted on the crane and rotatable around the fourth axis.

According to the medical imaging devices provided by the present disclosure, multi-angle and multi-position imaging requirements may be satisfied. In addition, the structures of the medical imaging devices provided by the present disclosure can be simple and reliable, which can not only improve the stability and mounting convenience but also reduce the cost.

The details of one or more embodiments of the subject matter described in the present disclosure are set forth in the accompanying drawings and description below. Other features, aspects, and advantages of the subject matter will become apparent from the description, the drawings, and the claims.

BRIEF DESCRIPTION OF DRAWINGS

FIG. 1b is a schematic diagram of a part of operating state of the medical imaging device shown in FIG. 1a.

FIG. 2b is a schematic diagram of a part of operating state of the medical imaging device shown in FIG. 2a.

FIG. 9b is a schematic diagram of a part of operating state of the medical imaging device shown in FIG. 9a.

FIG. 9c is a schematic diagram of a part of operating state of the medical imaging device shown in FIG. 9a.

DETAILED DESCRIPTION

Combining with a scanning bed system, an X-ray medical imaging device, such as an angiographic machine, may satisfy imaging requirements of various parts of a human body from different angles by being configured with a rotatable C-arm having an imaging system (hereinafter referred to as "an imaging chain") and a gantry capable of providing rotational or translational motion. According to mounting forms, the X-ray medical imaging device may be divided into two major forms: floor and suspension.

Figure 1A:
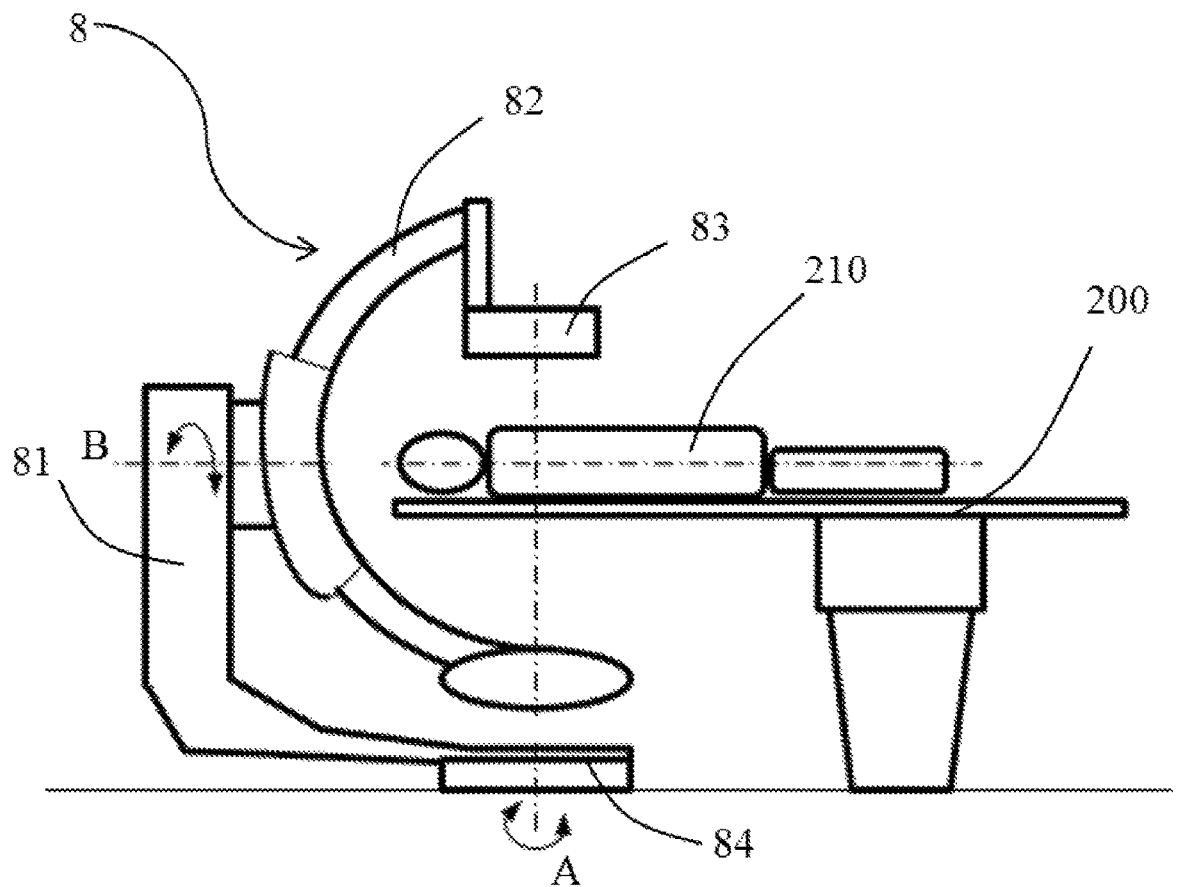
FIG. 1a is a structural schematic diagram of a medical imaging device.
Figure 1B:
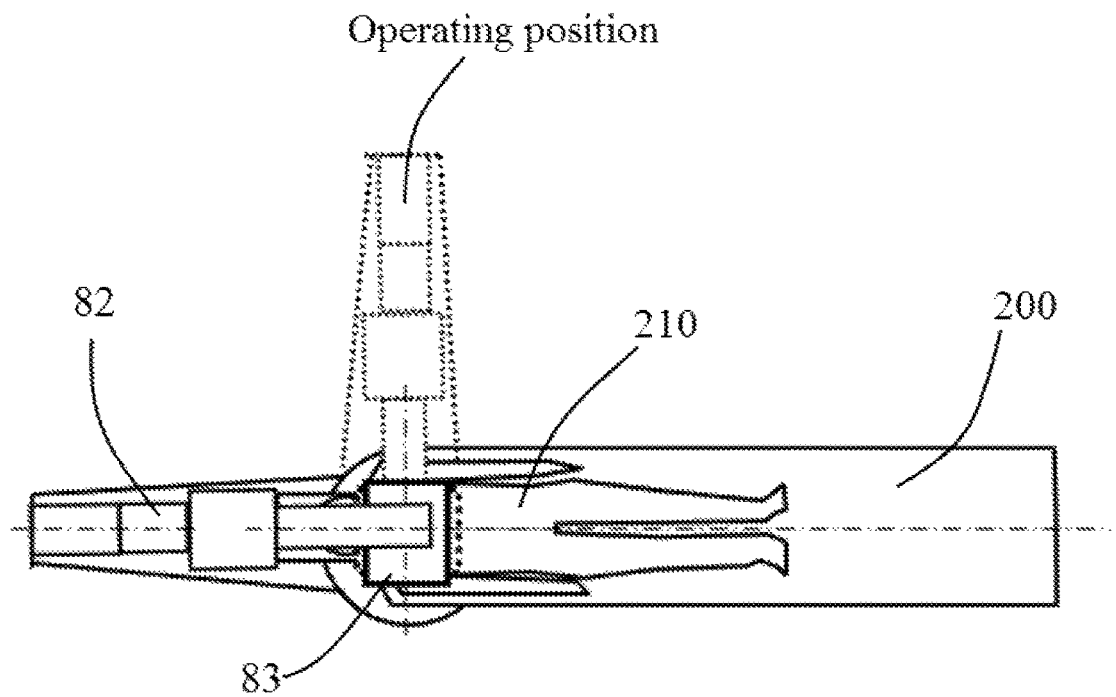

FIG. 1a is a structural schematic diagram of a medical imaging device. The following is described with an example of a floor angiographic machine 8. As shown in FIG. 1a, the floor angiographic machine 8 may include a floor gantry 81 and a rotatable C-arm 82 having an imaging chain 83. The rotatable C-arm 82 may be connected with the floor gantry 81. The floor gantry 81 may include a gantry base 84 which may be rotatable around an axis A. The rotatable C-arm 82 may be rotatable around an axis B. FIG. 1b shows a diagram from another perspective of view and a state diagram in an operating position of the floor angiographic machine 8 in FIG. 1a. The imaging chain 83 may check different positions of a subject 210 on a scanning bed 200 with the rotation of the gantry base 84 around the axis A and the rotation of the rotatable C-arm 82 around the axis B. Since the floor gantry 81 is in a fixed position and not moved, the floor angiographic machine 8 may limit possible footstep space for doctors and have high requirements on the floor load capacity.

Figure 2A:
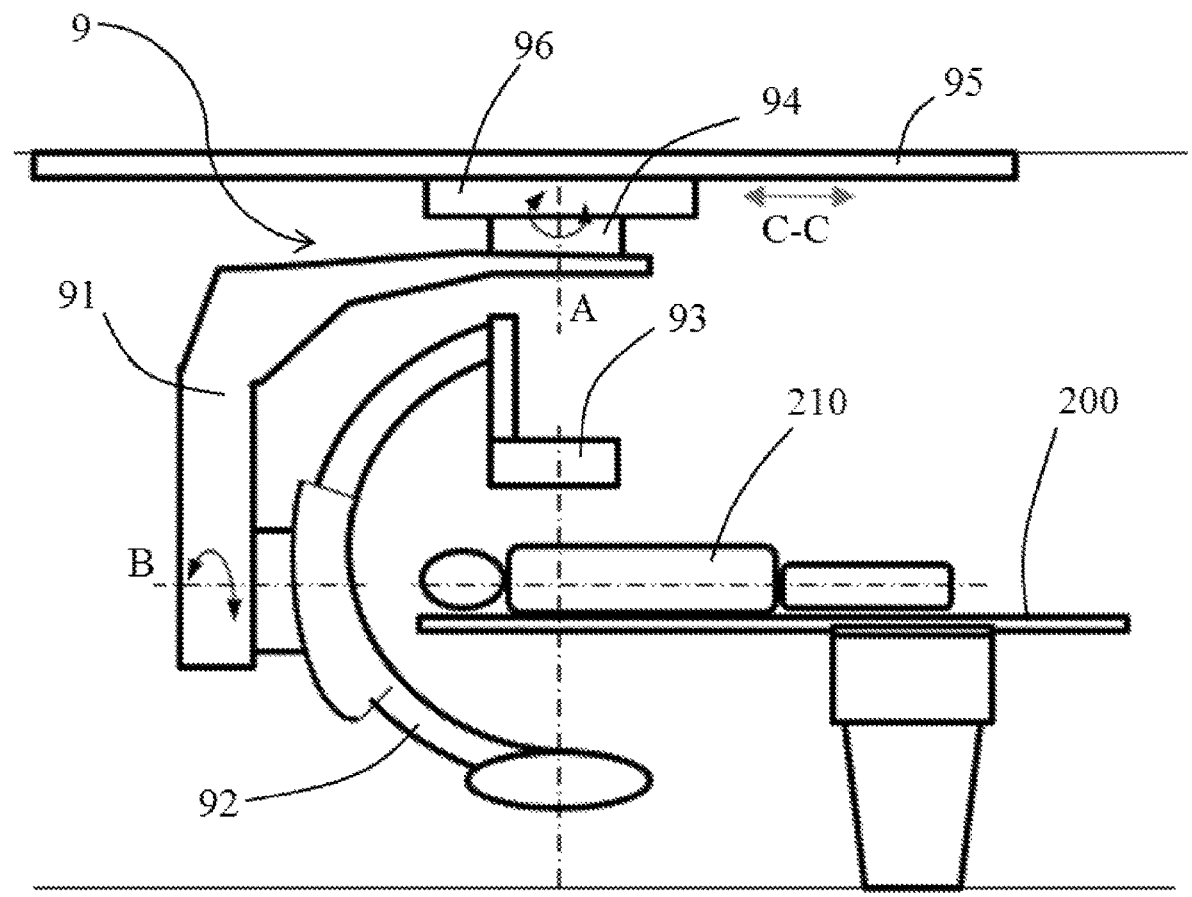
FIG. 2a is a structural schematic diagram of another medical imaging device.

FIG. 2a is a structural schematic diagram of another medical imaging device. The following is described with an example of a suspension angiographic machine 9. As shown in FIG. 2a, the suspension angiographic machine 9 may include a suspension gantry 91 and a rotatable C-arm 92 having an imaging chain 93. The rotatable C-arm 92 may be connected with the suspension gantry 91. The suspension gantry 91 may include a suspension base 94. The suspension base 94 may be provided at upper space where the suspension angiographic machine 9 is mounted, such as a roof or an upper steel beam of an operating room. The suspension base 94 may be rotatable around the axis A. The rotatable C-arm 92 may be rotatable around an axis B. In this way, the imaging chain 93 may check different positions of the subject 210 on the scanning bed 200 with the rotation of the suspension base 94 around the axis A and the rotation of the rotatable C arm 92 around the axis B.

Further, as shown in FIG. 2a, the suspension angiographic machine 9 may further include a guide rail 95 and a crane 96 to be mounted on the guide rail 95. The suspension base 94 may be mounted on the crane 96 by suspension. In this way, the movement of the imaging chain 93 in a direction C-C may be achieved.

Figure 2B:
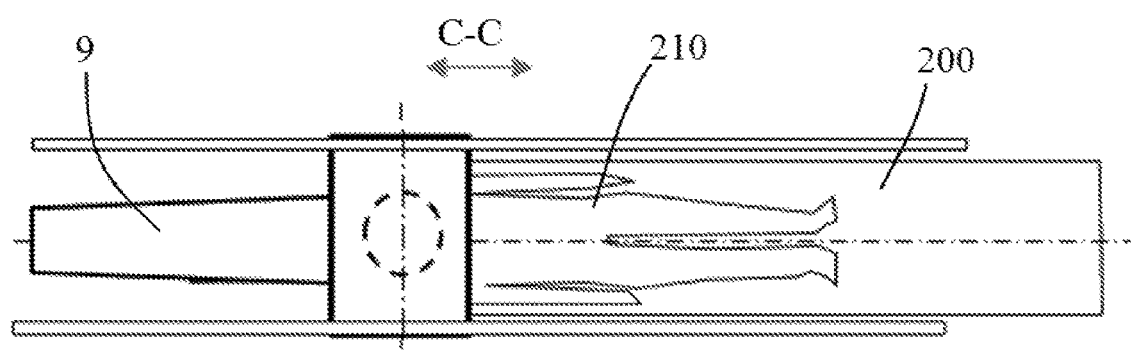

FIG. 2b shows a schematic diagram of a part of operating state of the suspension angiographic machine 9 shown in FIG. 2a. As shown in FIG. 2b, the imaging chain 93 may be moved in the direction C-C, and the movement space of the imaging chain 93 may be increased as compared to that shown in FIGS. 1a and 1b. Therefore, compared with the floor angiographic machine 8 in FIGS. 1a and 1b, the suspension angiographic machine 9 may have a greater degree of freedom, but the stability of the suspension angiographic machine 9 having the guide rail 95 may be poorer.

Although the suspension angiographic machine 9 has a larger footstep space than the floor angiographic machine 8, general imaging requirements of various body parts from a plurality of angles may be satisfied. However, with increasing clinical requirements, such as flexibility, stability and the like of the medical imaging device, new designs are needed for satisfying clinical requirements.

A floor industrial robotic arm may be used to grasp the rotatable C-arm and to move the rotatable C-arm to a different position or to arrange the rotatable C-arm at a different angle, thereby enhancing the flexibility of the angiographic machine. However, the design of utilizing the robotic arm is complex and costly.

Figure 3:
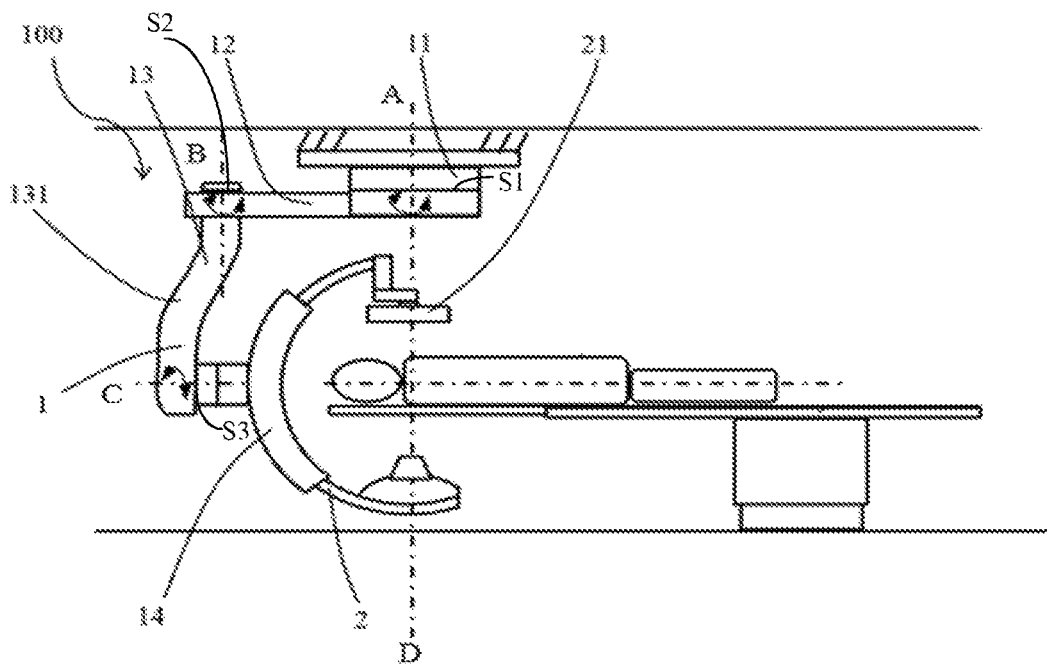
FIG. 3 is a structural schematic diagram of a medical imaging device according to an example of the present disclosure.

FIG. 3 is a structural schematic diagram of a medical imaging device 100 according to an example of the present disclosure. As shown in FIG. 3, the medical imaging device 100 according to the present disclosure includes a suspension gantry 1 and a rotatable C-arm 2 having an imaging chain 21. The rotatable C-arm 2 having the imaging chain 21 may be connected with the suspension gantry 1.

The suspension gantry 1 may include a suspension base 11 which is mounted on the top of an operating room such as a roof or an upper steel beam, etc., and a first rotating arm 12 connecting the suspension base 11. The first rotating arm 12 may be rotatable around a first axis A.

In an example, the first axis A may be located on a center line of the suspension base 11. The shape of the suspension base 11 may be cylindrical. The suspension base 11 may also have other shapes designed as desired, such as rectangular.

As shown in FIG. 3, the suspension gantry 1 may further include a second rotating arm 13 connecting the first rotating arm 12. The second rotating arm 13 may be rotatable around a second axis B. The second axis B and the first axis A are spaced with a distance. The distance can be pre-determined or pre-set. The first axis A is parallel to the second axis B.

In an example, the second rotating arm 13 may be connected to a first end of the first rotating arm 12 and the suspension base 11 is connected to a second end of the first rotating arm 12 which is opposite to the first end.

As shown in FIG. 3, the rotatable C-arm 2 may be connected with the second rotating arm 13. The rotatable C-arm 2 may be rotatable around a third axis C. The third axis C may be perpendicular to the first axis A and/or the second axis B.

In an example, the rotatable C-arm 2 may be connected with a first end of the second rotating arm 13 and the first rotating arm 12 is connected to a second end of the second rotating arm 13 which is opposite to the first end.

According to the above description, in an example, the first axis A may be disposed at the second end of the first rotating arm 12 and in a direction vertical to an interface S1 contacting the suspension base 11 and the first rotating arm 12. The suspension base 11 and the first rotating arm 12 may be rotatable around the first axis A, for example, rotatable on a horizontal plane perpendicular to the first axis A. The second axis B may be disposed at the first end of the first rotating arm 12 and also in a direction vertical to an interface contacting the second rotating arm 13 and the first rotating arm 12. The second rotating arm 13 may be rotatable around the second axis B, for example, rotatable on a horizontal plane perpendicular to the second axis B. The third axis C may be located in a direction vertical to an interface S3 contacting the second rotating arm 13 and the rotatable C-arm 2. The rotatable C-arm 2 may be rotatable around the third axis C, for example, rotatable on a vertical plane perpendicular to the third axis C.

Figure 4:
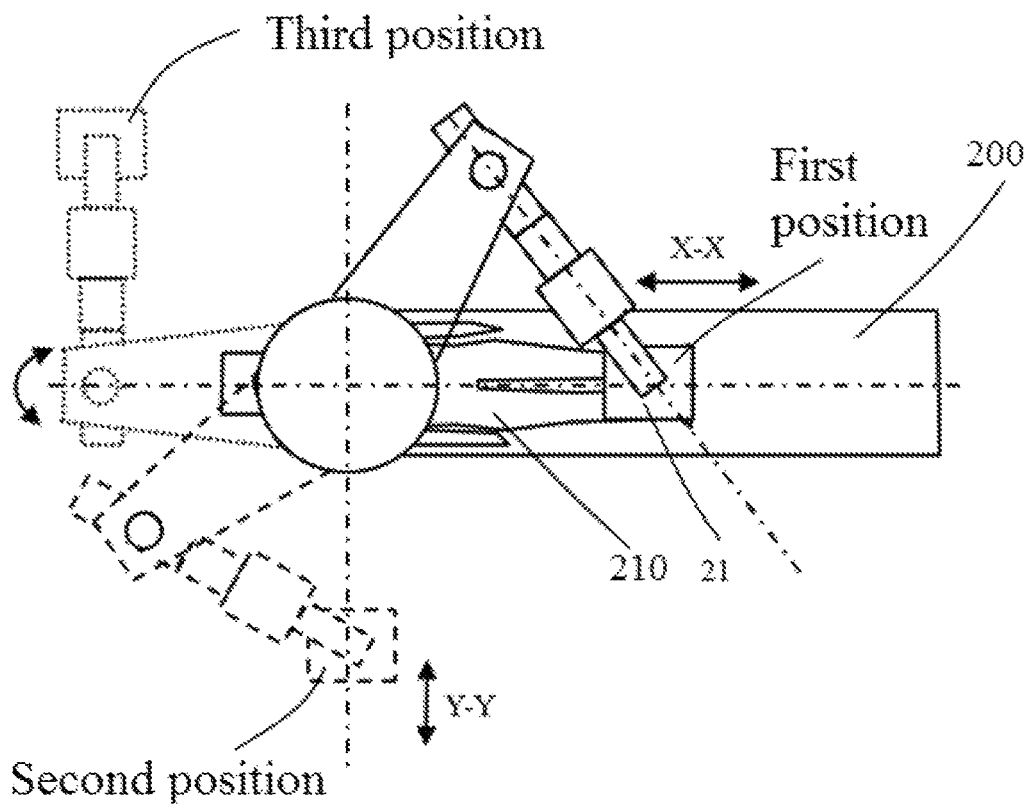
FIG. 4 is a schematic diagram of a part of operating state of the medical imaging device shown in FIG. 3.

FIG. 4 is a schematic diagram of a part of operating state of the medical imaging device 100 shown in FIG. 3. As shown in FIG. 4, translational movement of the imaging chain 21 in a direction X-X along the scanning bed 200 may be achieved by controlling rotation angles of the first axis A and the second axis B, as shown in a first position in FIG. 4. Translational movement of the imaging chain 21 in a direction Y-Y perpendicular to the scanning bed 200 may also be achieved by controlling the rotation angles of the first axis A, the second axis B and the third axis C, for example as shown in a second position in FIG. 4. In addition, when the medical imaging device 100 is unwanted, by controlling a rotation angle of the first axis A, the first rotating arm 12 may be caused to move the second rotating arm 13 to a position away from the scanning bed 200; in addition, the rotatable C-arm 2 may be moved to a position away from the scanning bed 200 by controlling a rotation angle of the second axis B, for example, as shown in a third position in FIG. 4. When the rotatable C-arm 2 is moved to a position away from the scanning bed 200, a larger surgical operating space may be provided. In this way, on one hand, multi-angle and multi-position imaging requirements may be satisfied. On the other hand, because the structure of the medical imaging device 100 provided in FIG. 3 is simple and reliable, not only the stability may be improved and it may be convenient to mount, but also the cost may be reduced.

As shown in FIG. 3, the suspension gantry 1 may further include a supporting arm 14 between the rotatable C-arm 2 and the second rotating arm 13. The rotatable C-arm 2 may be connected to the second rotating arm 13 via the supporting arm 14, and the supporting arm 14 may be rotatable around the third axis C.

Figure 5:
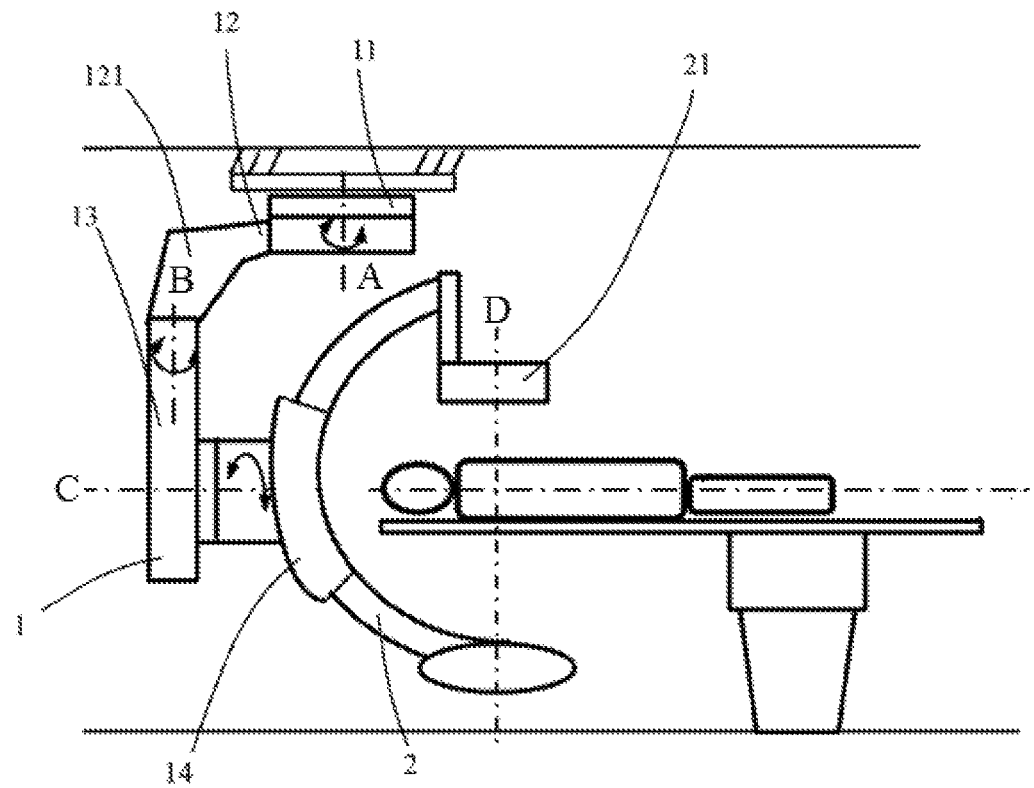
FIG. 5 is a structural schematic diagram of a medical imaging device according to another example of the present disclosure.

FIG. 5 is a structural schematic diagram of a medical imaging device according to another example of the present disclosure. As shown in FIG. 5, in an example, the first rotating arm 12 may include a first bending portion 121 between the first end and the second end of the first rotating arm 12, so that the rotatable C-arm 2 has a more free operation space. In another example, as shown in FIG. 3, the second rotating arm 13 may include a second bending portion 131 between the first end and the second end of the second rotating arm 13, so that the rotatable C-arm 2 has a more free operating space. When the second bending portion 131 is disposed or included in the second rotating arm 13, the bending moment subjected by the first axis A may be reduced. If the second bending portion 131 is not disposed or included in the second rotating arm 13, the second rotating arm 13 may be configured to be a structure without bending. In this case, the second axis B may be away from a center of gravity of the first rotating arm 12, so that the moment subjected by the first axis A becomes large. In still another example, the medical imaging device in the present disclosure may both have the first bending portion 121 and the second bending portion 131.

In another example of the present disclosure, the suspension gantry 1 may further include a third rotating arm (not shown). The rotatable C-arm 2 may be connected with the second rotating arm 13 through the third rotating arm. Alternatively, the rotatable C-arm 2 may be connected to the supporting arm 14 first, and then connected to the second rotating arm 13 via the third rotating arm. In other examples, the suspension gantry 1 may further include a fourth rotating arm, a fifth rotating arm, and the like. In the present disclosure, the rotatable C-arm 2 is connected with the second rotating arm 13, meaning that the rotatable C-arm 2 may be directly or indirectly connected with the second rotating arm 13.

Figure 6:
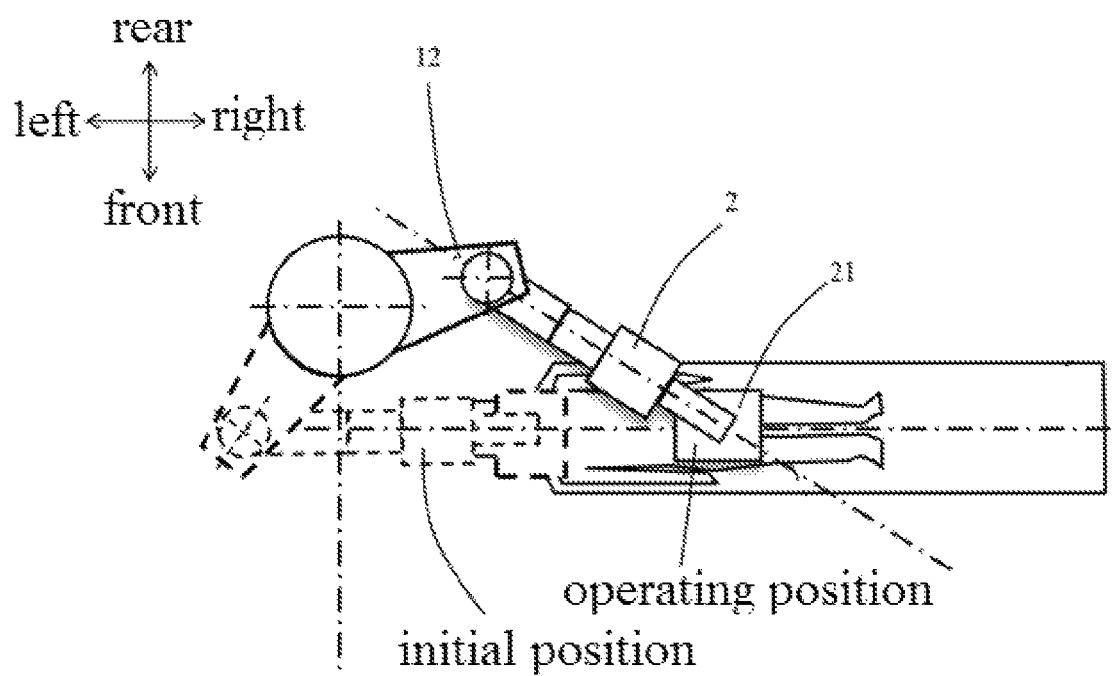
FIG. 6 is a schematic diagram of a part of operating state of the medical imaging device shown in FIG. 5.

In addition, in an example, the first axis A may be consistent with (or overlap) a center line D of the imaging chain 21 which is mounted on the rotatable C-arm 2 at an initial position (as shown in FIG. 3). In another example, the first axis A and the center line D of the imaging chain 21 are spaced with a distance at the initial position (the initial position shown in FIG. 5 and the initial position shown in FIG. 6). The present disclosure defines front, rear, left and right directions in FIG. 6. The first axis A and the center line D of the imaging chain 21 may be spaced with a distance in the front-rear direction and/or the left-right direction, respectively. In this way, the range of motion of the first rotating arm 12 and the second rotating arm 13 is greater, and a greater operating space may be provided.

Figure 7:
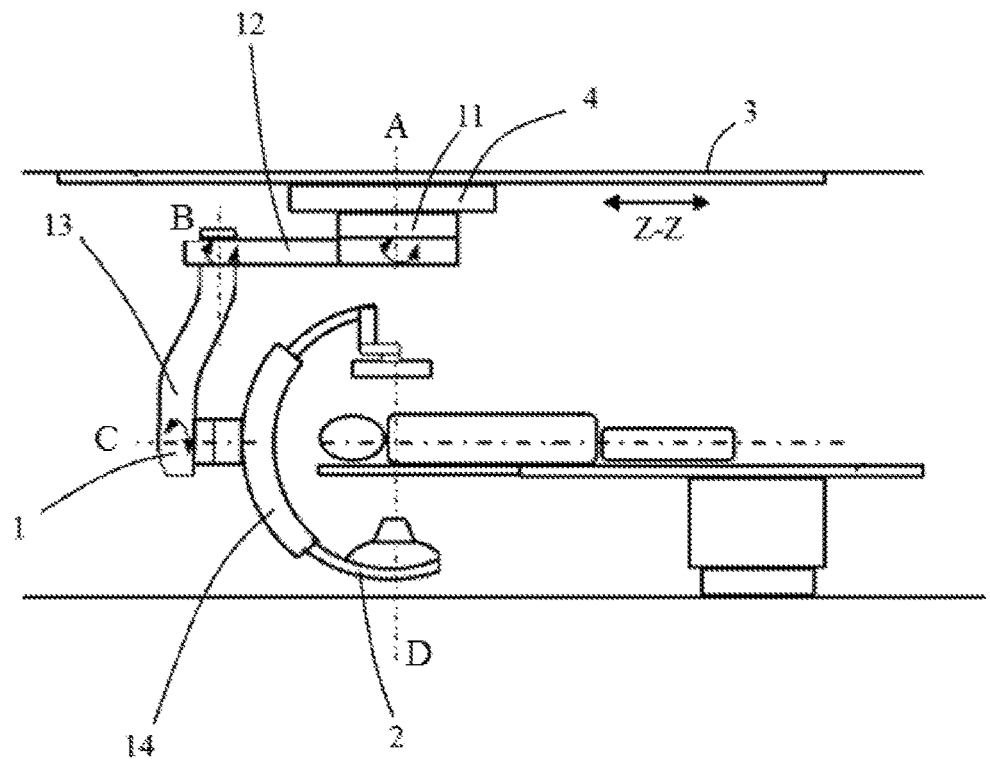
FIG. 7 is a structural schematic diagram of a medical imaging device according to still another example of the present disclosure.

FIG. 7 is a structural schematic diagram of a medical imaging device according to still another example of the present disclosure. As shown in FIG. 7, on the basis of examples described above, the suspension gantry 1 may further include a guide rail 3 and a crane 4. The guide rail 3 is mounted on the top of the operating room. The crane 4 is mounted on the guide rail 3 and moved along the guide rail 3. The suspension base 11 may be mounted on the crane 4. In this way, in addition to enabling the medical imaging device to obtain the range of motion described in the examples described above, it is possible to additionally move the medical image device in a direction Z-Z.

Figure 8:
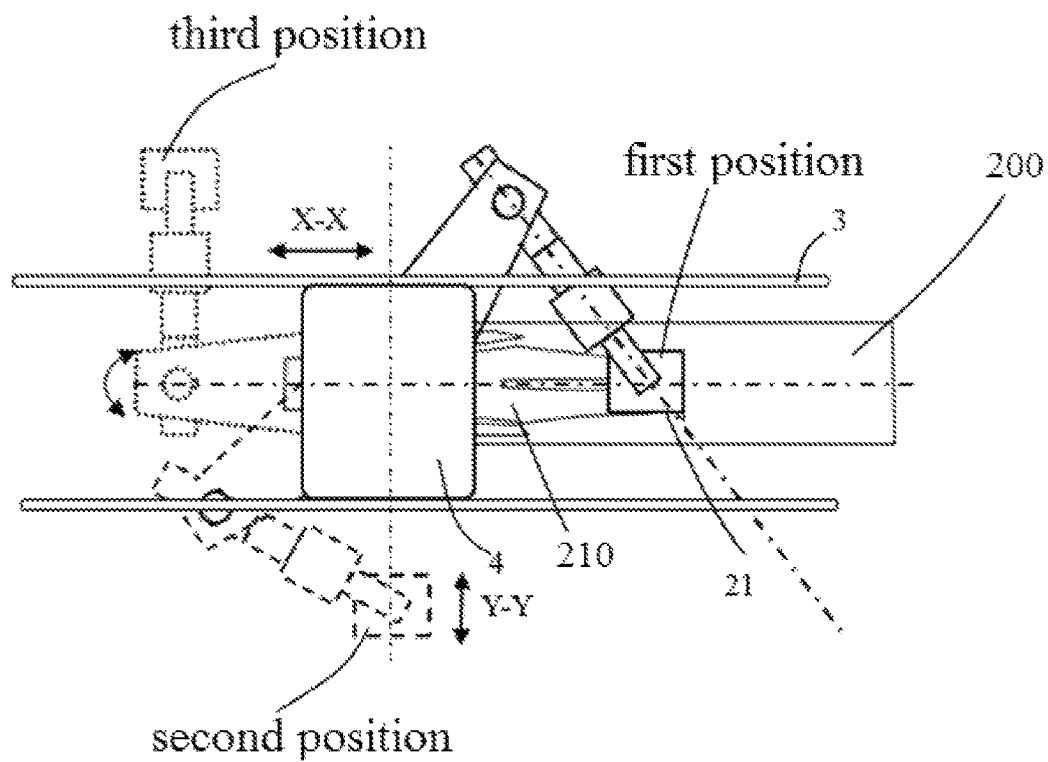
FIG. 8 is a schematic diagram of a part of operating state of the medical imaging device shown in FIG. 7.

FIG. 8 is a schematic diagram of a part of operating state of the medical imaging device shown in FIG. 7. As shown in the first position in FIG. 8, translational movement of the imaging chain 21 in the direction X-X along the scanning bed 200 may be achieved by controlling rotation angles of the first axis A and the second axis B and controlling the movement of the crane 4 on the guide rail 3, where the direction X-X may be consistent with the direction Z-Z in FIG. 7. Thus, in this example, the imaging chain 21 may obtain a larger translation distance in the direction X-X (or the direction Z-Z). The translational movement of the imaging chain 21 in the direction Y-Y perpendicular to the scanning bed 200 may also be achieved by controlling the rotation angles of the first axis A, the second axis B and the third axis C, for example as shown in the second position in FIG. 8. In addition, when the medical imaging device is unwanted, by controlling a rotation angle of the first axis A, the first rotating arm 12 may be caused to move the second rotating arm 13 to a position away from the scanning bed 200. The rotatable C-arm 2 may be moved to a position away from the scanning bed 200 by controlling the rotation angle of the second axis B, for example, as shown in the third position in FIG. 8. When the rotatable C-arm 2 is moved to a position away from the scanning bed 200, a larger surgical operating space may be provided. Thus, the imaging chain 21 may get a greater range of motion around the scanning bed 200, and more advanced clinical application requirements may be satisfied. Rotating control for the first axis A and the second axis B may be electric or may be partially or entirely manual.

Figure 9A:
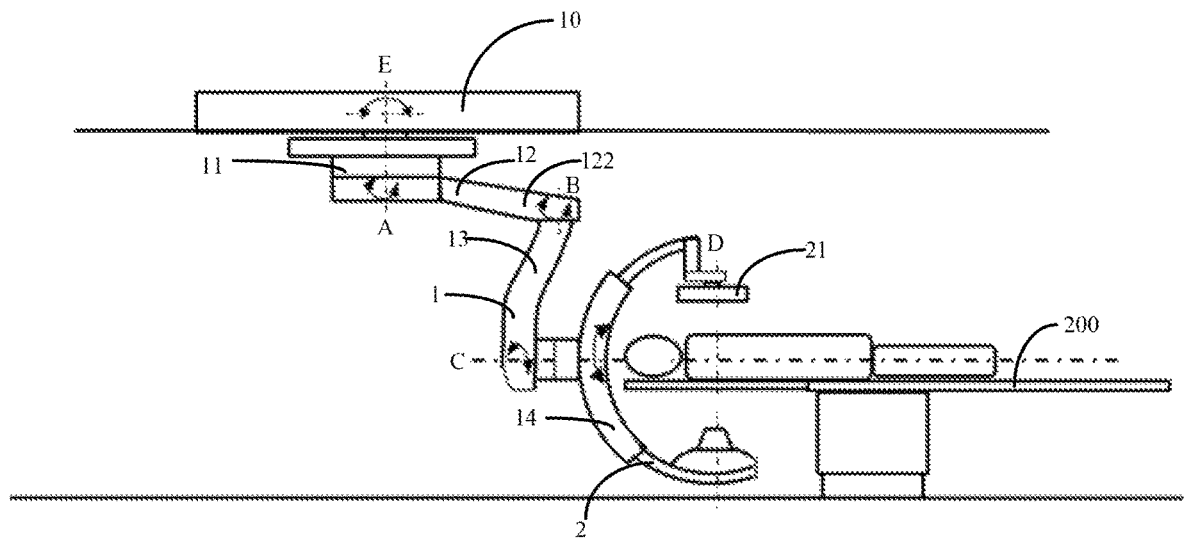
FIG. 9a is a structural schematic diagram of a medical imaging device according to still another example of the present disclosure.

FIG. 9a is a structural schematic diagram of a medical imaging device according to still another example of the present disclosure. As shown in FIG. 9a, the suspension gantry 1 may further include a supporting base 10, such as a steel beam base 10. The suspension base 11 may be mounted on the steel beam base 10. The suspension base 11 may be rotatable around a fourth axis E that can be a shaft.

Figure 9B:
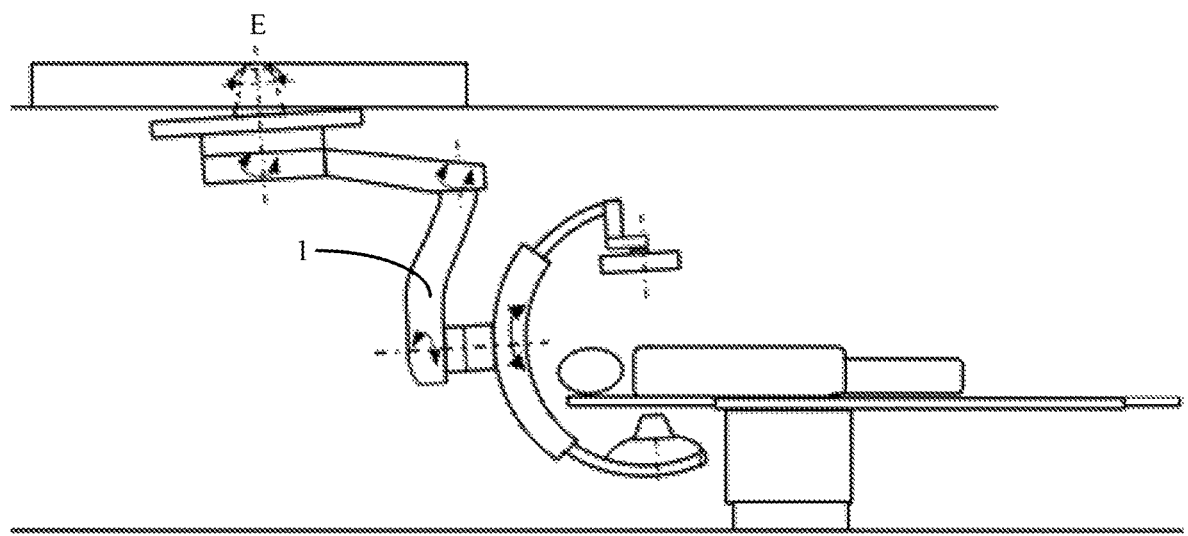

In an example, the fourth axis E may be disposed at a first end of the suspension base 11 and the first rotating arm 12 is connected to a second end of the suspension base 11 which is opposite to the first end. FIG. 9b is a schematic diagram of the medical imaging device shown in FIG. 9a after being rotated around the fourth axis E by an angle. The fourth axis E may be parallel to a ceiling, thereby achieving the movement of the suspension gantry 1 in the front-rear direction and/or the left-right direction as defined in FIG. 6. The fourth axis E may be configured to adjust the posture of the suspension gantry to improve the imaging precision of the imaging chain 21.

In an example, the first rotating arm 12 may further include an inclined portion 122. The inclined portion 122 may incline from an end of the first rotating arm 12 to which the suspension base 11 is connected towards another end of the first rotating arm 12 to which the second rotating arm 13 is connected. As compared with a first rotating arm without an inclined portion, a distance between the first rotating arm 12 having the inclined portion 122 and the upper space becomes larger, thereby facilitating the maintenance of components in the suspension base 11 such as a motor, a speed reducer, a potentiometer, a cable and the like.

Figure 9C:
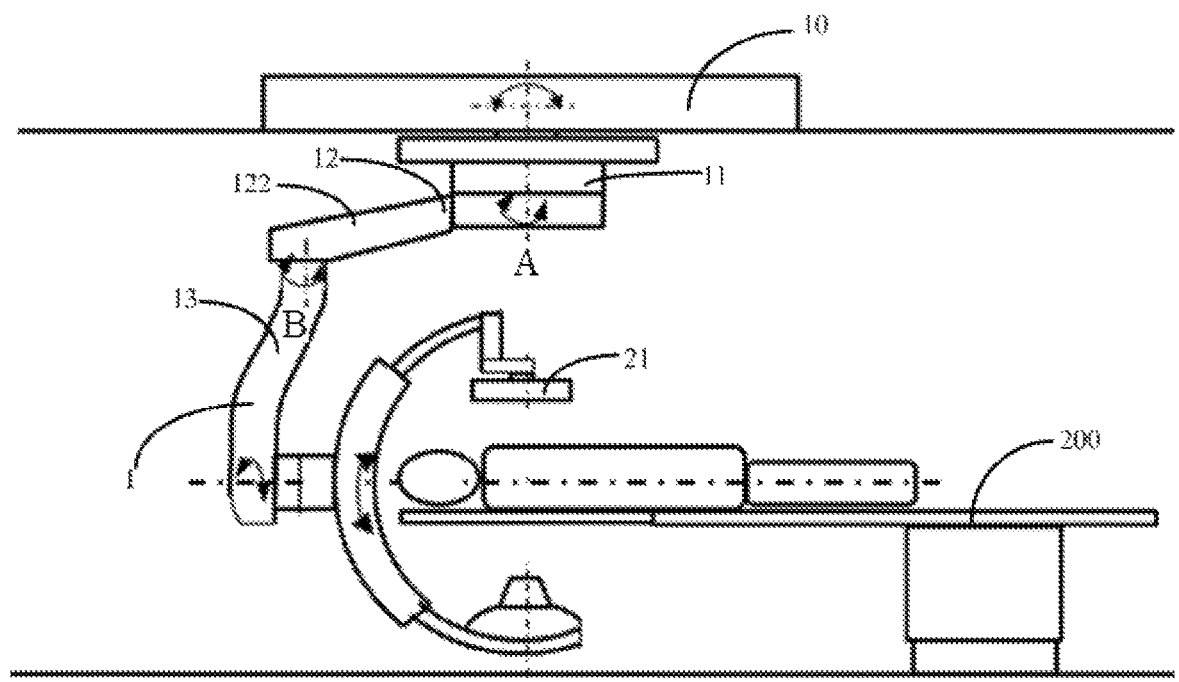

FIG. 9c is a schematic diagram of a part of operating state of the medical imaging device shown in FIG. 9a. The scanning bed 200 may move in a direction parallel to the ground. From the position shown in FIG. 9a, the operating state shown in FIG. 9c may be obtained by moving the scanning bed 200 and rotating the suspension gantry 1 around the first axis A and the second axis B by an angle, for example, 180°.

Figure 9D:
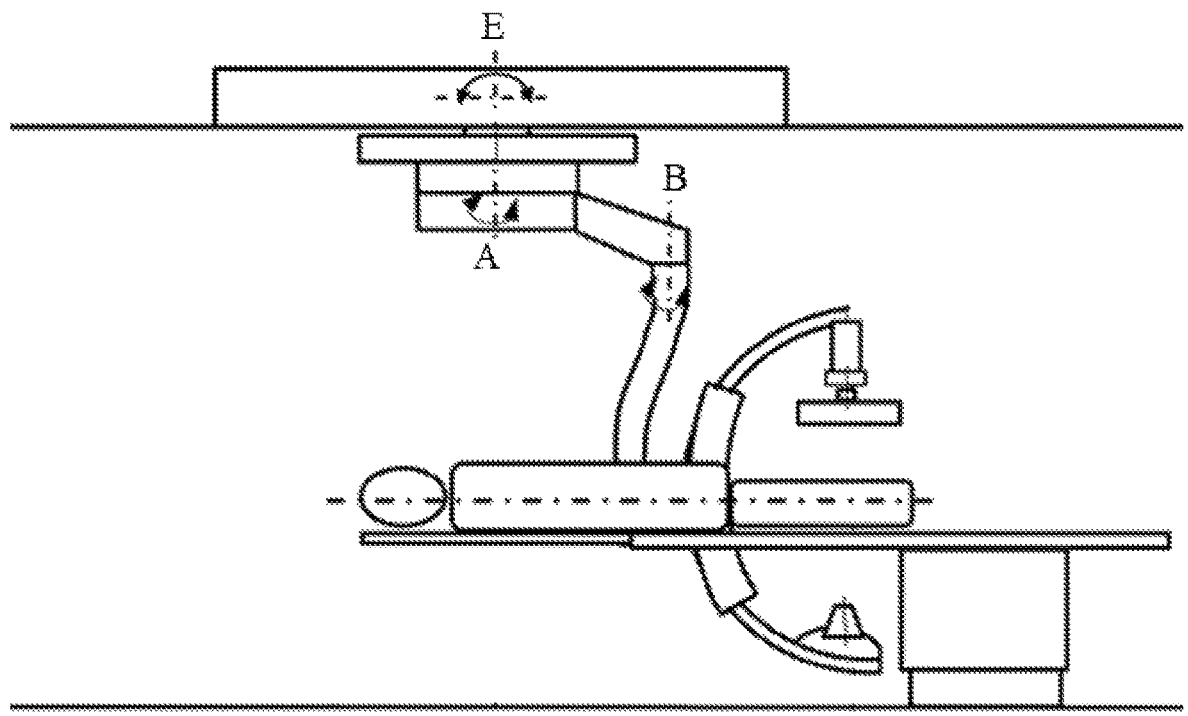
FIG. 9d is a schematic diagram of a part of operating state of the medical imaging device shown in FIG. 9c.

FIG. 9d is a schematic diagram of a part of operating state of the medical imaging device shown in FIG. 9c. The operating state may be obtained after the suspension gantry 1 in FIG. 9c rotates around the first axis A and the second axis B by an angle, for example, 180°.

Figure 10A:
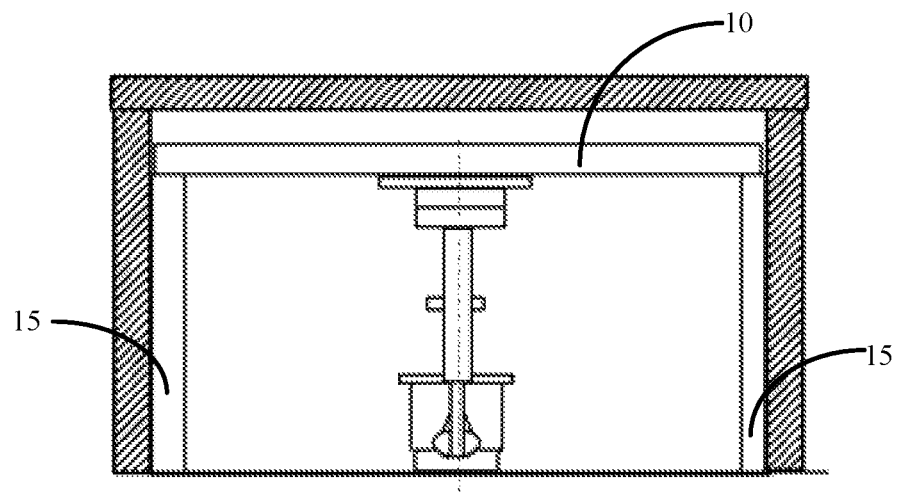
FIG. 10a is a schematic diagram of a method of mounting a suspension gantry according to an example of the present disclosure.

FIG. 10a is a schematic diagram of a method of mounting a suspension gantry according to an example of the present disclosure. The suspension gantry 1 may also include a supporting frame, such as a vertical beam 15, for mounting the supporting base, such as the steel beam base 10. The steel beam base 10 may be disposed on the vertical beam 15. The vertical beam 15 may be disposed close to the wall. In this way, it is unnecessary to mount the steel beam base 10 to the ceiling and the wall, and thus there is no load bearing requirement for the ceiling and the wall.

Figure 10B:
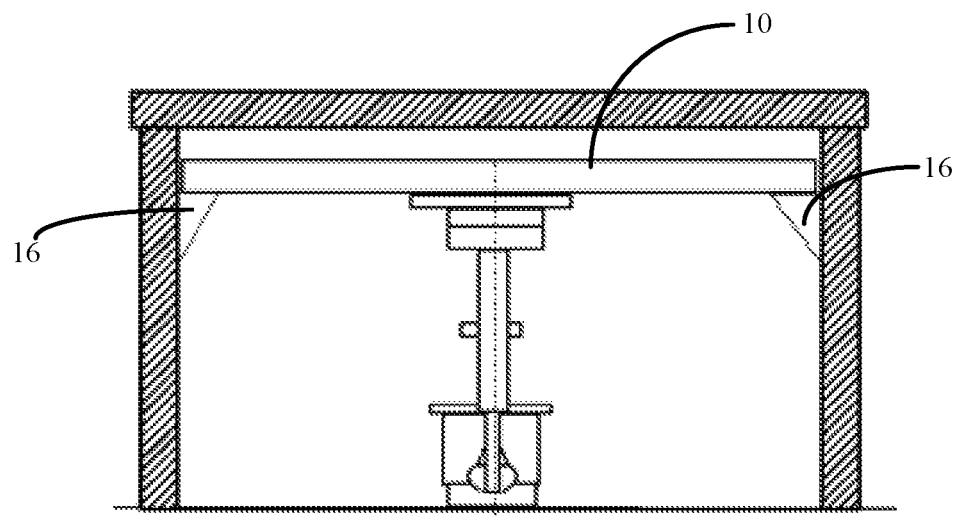
FIG. 10b is a schematic diagram of a method of mounting a suspension gantry according to another example of the present disclosure.

FIG. 10b is a schematic diagram of a method of mounting a suspension gantry according to another example of the present disclosure. The suspension gantry 1 may further include a support 16 as the above supporting frame. The steel beam base 10 may be disposed on the support 16. The support 16 may be disposed on the wall. In this way, it is unnecessary to mount the steel beam base 10 to the ceiling and the wall, and there is no load bearing requirement for the ceiling and the wall.

Figure 10C:
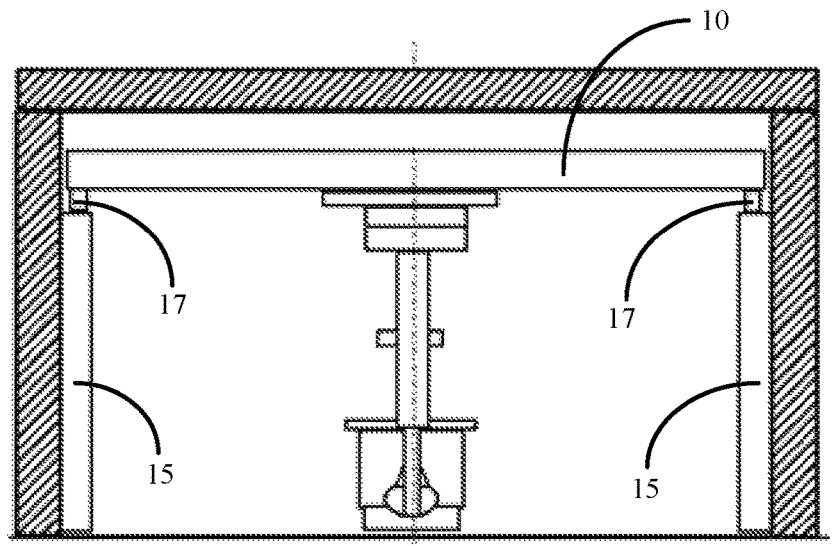
FIG. 10c is a schematic diagram of a method of mounting a suspension gantry according to still another example of the present disclosure.

As shown in FIG. 10c, a height adjusting device 17 may be provided between the steel beam base 10 and the vertical beam 15 on the basis of the above FIG. 10a to adjust height of the entire suspension gantry. The height adjusting device 17 may be an electric, hydraulic or manual lifting device or the like.

In an example, a height adjusting device may also be provided between the steel beam base 10 and the support 16 to adjust the height of the entire suspension gantry. The height adjusting device may be an electric, hydraulic or manual lifting device or the like.

Figure 11A:
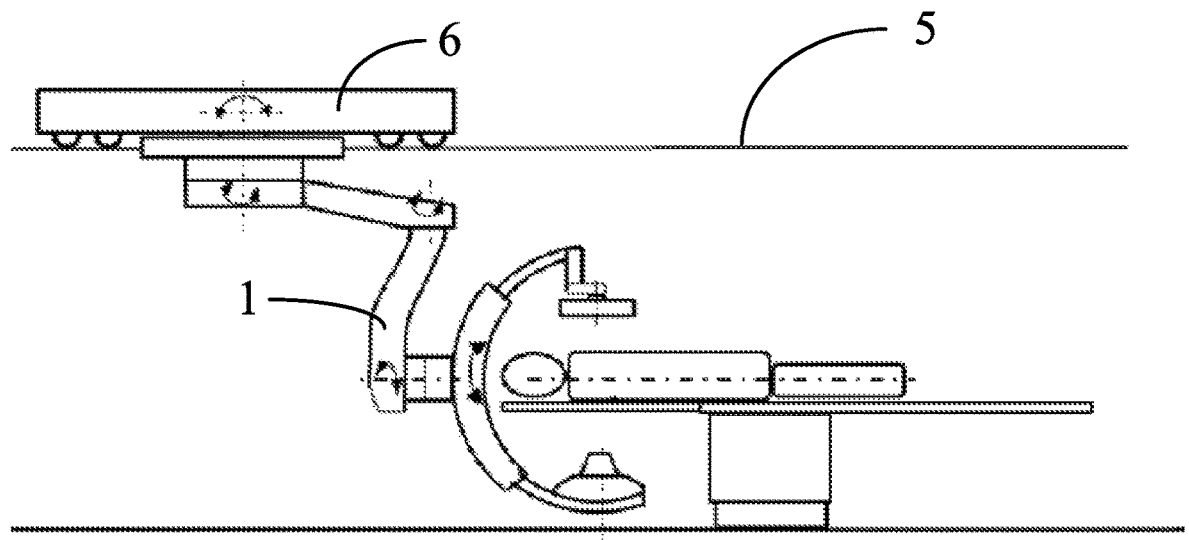
FIG. 11a is a structural schematic diagram of a medical imaging device according to still another example of the present disclosure.
Figure 11B:
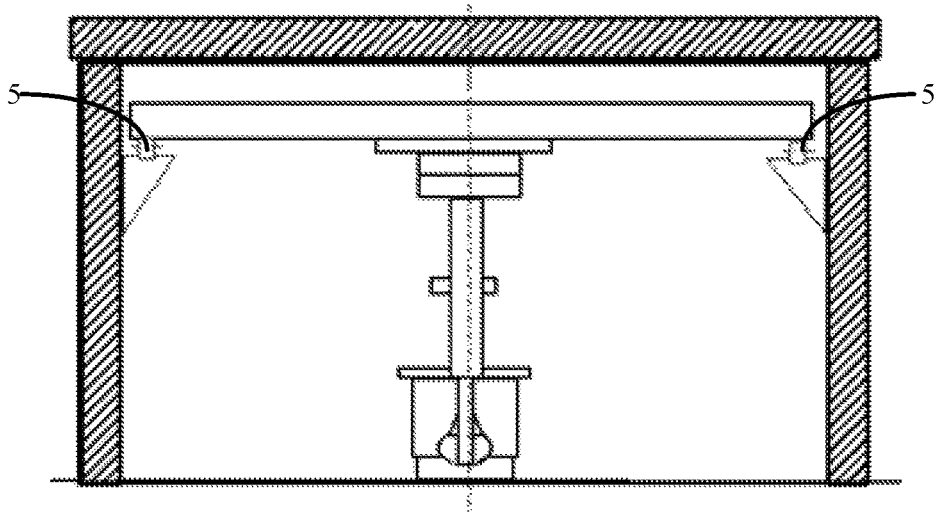
FIG. 11b is a schematic view of the medical imaging device shown in FIG. 11a from another perspective of view.

FIG. 11a is a structural schematic diagram of a medical imaging device according to still another example of the present disclosure. FIG. 11b is a schematic view of the medical imaging device shown in FIG. 11a from another perspective of view. As shown in FIG. 11a, on the basis of FIGS. 10a and 10b, the suspension gantry 1 may further include a guide rail 5 and a wheel set. The guide rail 5 is mounted on the vertical beam or the support. The wheel set is mounted on the guide rail 5 and moved along the guide rail 5. The steel beam base 10 and the wheel set may form a crane 6. The suspension base 11 may be mounted on the crane 6 and rotatable around the fourth axis E. In this way, in addition to enabling the medical imaging device shown in FIG. 11a and FIG. 11b to obtain the range of motion described in examples described above, it is possible to additionally move the medical image device in the direction Z-Z.

Figure 12:
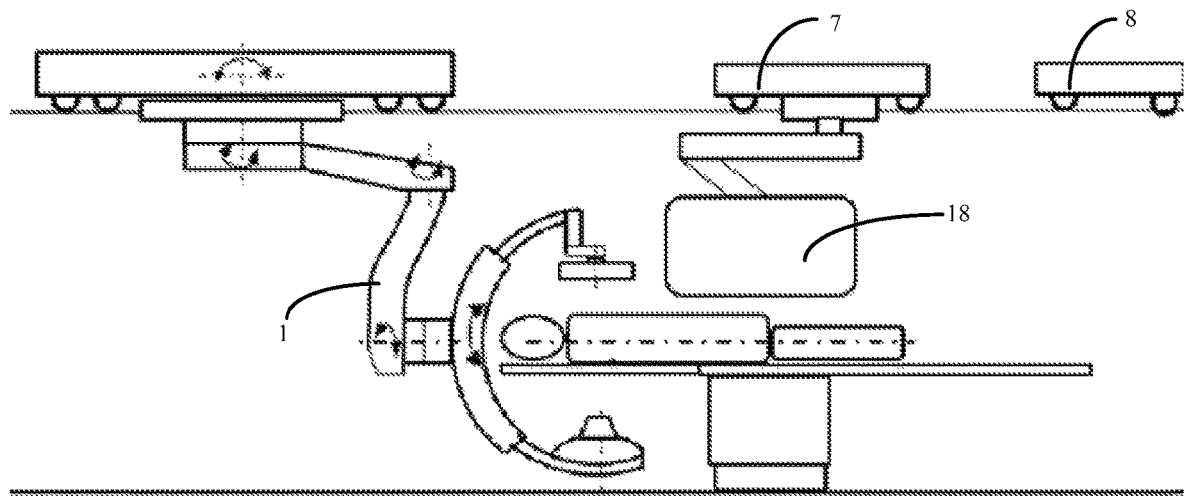
FIG. 12 is a structural schematic diagram of a medical imaging device according to still another example of the present disclosure.

As shown in FIG. 12, the suspension gantry 1 may further include other cranes, such as a crane 7, a crane 8, and the like. The other cranes may be configured to mount a surgically assisting device, such as a display device 18 and the like.

The suspension gantry 1 described above may contain a plurality of degrees of freedom for movement, and there may be a compound movement between the plurality of rotation axes. For example, the suspension gantry may have a translational movement in the directions X-X and Y-Y by rotating around the first axis A and the second axis B. In addition, there may be a collision between a crane and another crane and between a device and a person. A motion anti-collision device and a sensor may be mounted to ensure safety. In order to achieve the compound motion and ensure safety, a motion control system of the suspension gantry 1 needs a higher movement precision and a situation processing ability, so as to ensure a multi-axis linkage effect and achieve a real-time multi-axis high-precision motion control.

In the foregoing description, details of technical solutions of the present disclosure have been set forth. However, those skilled in the art will recognize that the present disclosure is not limited to the specific details set forth in the above examples, but may change within the scope defined by the claims.

The foregoing is intended only as a preferred example of the present disclosure and is not intended to be limiting of the present disclosure, and any modifications, equivalent substitutions, improvements and the like within the spirit and principle of the present disclosure are intended to be included within the scope of protection of the present disclosure.

The invention claimed is:

1. A suspension gantry comprising:
   a suspension base;
   a first rotating arm configured to be connected to the suspension base and rotatable around a first axis; and
   a second rotating arm configured to be connected to the first rotating arm and rotatable around a second axis,
   wherein the second rotating arm is configured to be connected with a rotatable C-arm, which is rotatable around a third axis,
   wherein the first rotating arm comprises an inclined portion that inclines from an end of the first rotating arm to which the suspension base is connected towards another end of the first rotating arm to which the second rotating arm is connected.

2. The suspension gantry according to claim 1, further comprising:
   a first interface contacting the first rotating arm and the suspension base;
   a second interface contacting the second rotating arm and the first rotating arm; and
   a third interface contacting the rotatable C-arm and the second rotating arm, wherein, the first axis is the first interface contacting the first rotating arm and the suspension base;
   the second axis is the second interface contacting the second rotating arm and the first rotating arm;
   the second rotating arm is connected to a first end of the first rotating arm and the suspension base is connected to a second end of the first rotating arm which is opposite to the first end;
   the first axis and the second axis are spaced with a distance;
   the third axis is perpendicular the third interface contacting the rotatable C-arm and the second rotating arm;
   the rotatable C-arm is connected to a first end of the second rotating arm and the first rotating arm is connected to a second end of the second rotating arm which is opposite to the first end;
   the first axis is parallel to the second axis; and
   the third axis is perpendicular to the first axis and the second axis.

3. The suspension gantry according to claim 1, further comprising:
   a guide rail mounted on a top of an operating room; and
   a crane mounted on the guide rail and configured to be movable along the guide rail, the suspension base being mounted on the crane.

4. The suspension gantry according to claim 1, further comprising a supporting base, wherein the suspension base is mounted on the supporting base and rotatable around a fourth axis.

5. The suspension gantry according to claim 4, wherein,
   the fourth axis is disposed at a first end of the suspension base and the first rotating arm is connected to a second end of the suspension base which is opposite to the first end; and
   a plane in which the fourth axis is located is perpendicular to the first axis.

6. The suspension gantry according to claim 4, further comprising a supporting frame, wherein the supporting base is mounted on the supporting frame.

7. The suspension gantry according to claim 6, further comprising a height adjusting device disposed between the supporting base and the supporting frame.

8. The suspension gantry according to claim 6, further comprising:
a guide rail mounted at an upper end of the supporting frame; and
a wheel set mounted on the guide rail and configured to be movable along the guide rail, the supporting base and the wheel set forming a crane, the suspension base being mounted on the crane and rotatable around the fourth axis.

9. The suspension gantry according to claim 1, wherein the second rotating arm comprises a bending portion between a first end and a second end of the second rotating arm.

10. A suspension gantry comprising:
a suspension base;
a first rotating arm configured to be connected to the suspension base and rotatable around a first axis;
a second rotating arm configured to be connected to the first rotating arm and rotatable around a second axis, wherein the second rotating arm is configured to be connected with a rotatable C-arm, which is rotatable around a third axis; and
a supporting base, wherein the suspension base is mounted on the supporting base and rotatable around a fourth axis.

11. The suspension gantry according to claim 10, wherein the fourth axis is disposed at a first end of the suspension base and the first rotating arm is connected to a second end of the suspension base which is opposite to the first end, and
wherein a plane in which the fourth axis is located is perpendicular to the first axis.

12. A medical imaging device, comprising:
a suspension gantry comprising:
a suspension base;
a first rotating arm configured to be connected to the suspension base and rotatable around a first axis; and
a second rotating arm configured to he connected to the first rotating arm and rotatable around a second axis; and
a rotatable C-arm configured to be connected with the second rotating arm and rotated around a third axis, the rotatable C-arm comprising an imaging chain,
wherein the first rotating arm comprises an inclined portion that inclines from an end of the first rotating arm to which the suspension base is connected towards another end of the first rotating arm to which the second rotating arm is connected.

13. The medical imaging device according to claim 12, further comprising:
a first interface contacting the first rotating arm and the suspension base;
a second interface contacting the second rotating arm and the first rotating arm; and
a third interface contacting the rotatable C-arm and the second rotating arm,
wherein, the first axis is the first interface contacting the first rotating arm and the suspension base;
the second axis is the second interface contacting the second rotating arm and the first rotating arm;
the second rotating arm is connected to a first end of the first rotating arm and the suspension base is connected to a second end of the first rotating arm which is opposite to the first end;
the first axis and the second axis are spaced with a distance;
the third axis is the third interface contacting the rotatable C-arm and the second rotating arm;
the rotatable C-arm is connected to a first end of the second rotating arm and the first rotating arm is connected to a second end of the second rotating arm which is opposite to the first end;
the first axis is parallel to the second axis; and
the third axis is perpendicular to the first axis and the second axis.

14. The medical imaging device according to claim 12, wherein the suspension gantry further comprises:
a guide rail mounted on a top of an operating room; and
a crane mounted on the guide rail and configured to be movable along the guide rail, the suspension base being mounted on the crane.

15. The medical imaging device according to claim 12, wherein,
the suspension gantry further comprises a supporting base, and
the suspension base is mounted on the supporting base and rotatable around a fourth axis.

16. The medical imaging device according to claim 15, wherein,
the fourth axis is disposed at a first end of the suspension base and the first rotating arm is connected to a second end of the suspension base which is opposite to the first end; and
a plane in which the fourth axis is located is perpendicular to the first axis.

17. The medical imaging device according to claim 15, wherein,
the suspension gantry further comprises a supporting frame, and
the supporting base is mounted on the supporting frame.

18. The medical imaging device according to claim 17, wherein the suspension gantry further comprises:
a height adjusting device disposed between the supporting base and the supporting frame.

19. The medical imaging device according to claim 17, wherein the suspension gantry further comprises:
a guide rail mounted at an upper end of the support frame; and
a wheel set mounted on the guide rail and configured to be movable along the guide rail, the supporting base and the wheel set forming a crane, the suspension base being mounted on the crane and rotatable around the fourth axis.

20. The medical imaging device according to claim 12, wherein the second rotating arm comprises a bending portion between a first end and a second end of the second rotating arm.

* * * * *